United States Patent
Bogle

(10) Patent No.: US 10,300,163 B2
(45) Date of Patent: May 28, 2019

(54) MOISTURE ABSORBENT AND DECONTAMINANT

(71) Applicant: Peter Andrew Bogle, St. Charles, IL (US)

(72) Inventor: Peter Andrew Bogle, St. Charles, IL (US)

(*) Notice: Subject to any disclaimer, the term of this patent is extended or adjusted under 35 U.S.C. 154(b) by 97 days.

(21) Appl. No.: 15/412,258

(22) Filed: Jan. 23, 2017

(65) Prior Publication Data

US 2017/0210541 A1 Jul. 27, 2017

Related U.S. Application Data

(60) Provisional application No. 62/281,401, filed on Jan. 21, 2016.

(51) Int. Cl.
| B01J 20/26 | (2006.01) |
| A61L 9/014 | (2006.01) |
| B01J 20/28 | (2006.01) |

(52) U.S. Cl.
CPC ............ *A61L 9/014* (2013.01); *B01J 20/262* (2013.01); *B01J 20/2805* (2013.01); *B01J 20/28016* (2013.01); *A61L 2209/131* (2013.01); *A61L 2209/22* (2013.01)

(58) Field of Classification Search
CPC ........ A01N 55/02; A61L 9/014; B01J 20/262; B01J 20/28016; B01J 20/2805; B65D 65/40; B65D 81/264; B65D 81/28
USPC ........ 96/222, 226; 261/DIG. 88; 422/1, 4, 5, 422/120, 122
See application file for complete search history.

(56) References Cited

U.S. PATENT DOCUMENTS

| 4,534,775 A * | 8/1985 | Frazier ................... B01D 53/00 422/122 |
| 4,604,110 A * | 8/1986 | Frazier ...................... A61L 9/00 422/122 |
| 5,874,052 A * | 2/1999 | Holland .................. B01D 46/12 422/122 |
| 6,190,437 B1 * | 2/2001 | Forsyth .............. B01D 46/0028 210/501 |
| 8,911,678 B2 * | 12/2014 | Mirowski ............... A61L 9/014 239/34 |
| 2002/0141898 A1 * | 10/2002 | Carlucci .................... A61L 9/01 422/5 |
| 2003/0194516 A1 * | 10/2003 | Payne .................. B01D 53/261 428/35.7 |
| 2014/0157990 A1 * | 6/2014 | Piry .................... B01D 46/0028 96/226 |
| 2017/0217661 A1 * | 8/2017 | Erickson .............. B65D 81/264 |

* cited by examiner

*Primary Examiner* — Frank M Lawrence, Jr.
(74) *Attorney, Agent, or Firm* — Dunlap Bennett & Ludwig PLLC

(57) ABSTRACT

A moisture absorbent and decontaminant is provided. The moisture absorbent and decontaminant includes a receptacle. The receptacle is formed of a permeable material having a plurality of pores. The present invention includes at least first pellets, second pellets and third pellets. The pellets are enclosed within the receptacle. The pellets include a diameter larger than the diameter of the pores and thereby cannot escape the receptacle. The first pellets include an antimicrobial. The second pellets include an antifungal. The third pellets include a moisture absorber.

13 Claims, 1 Drawing Sheet

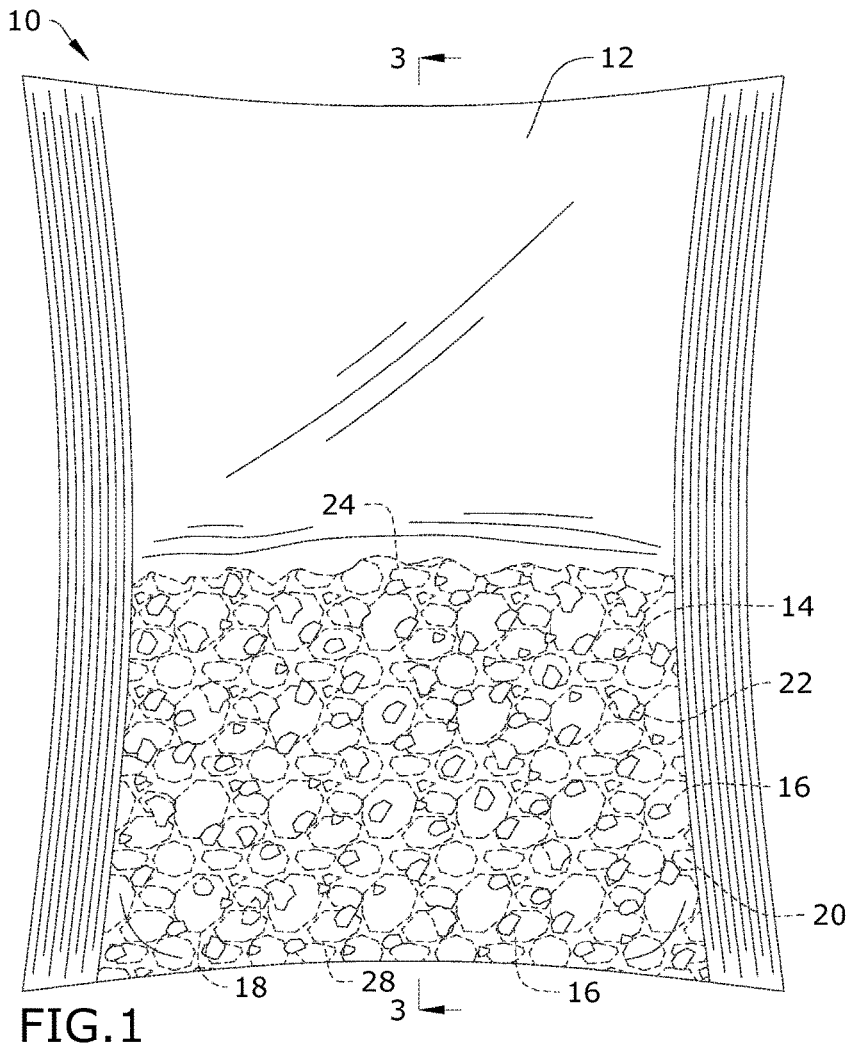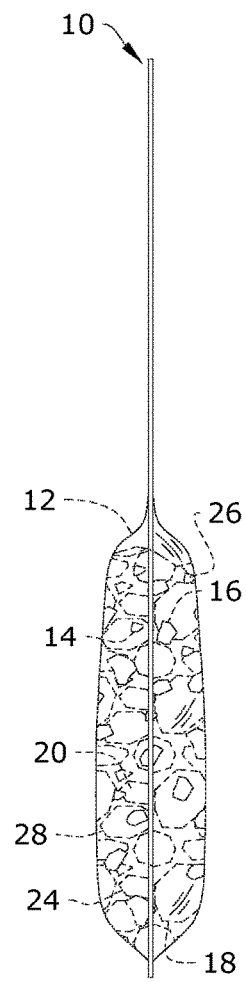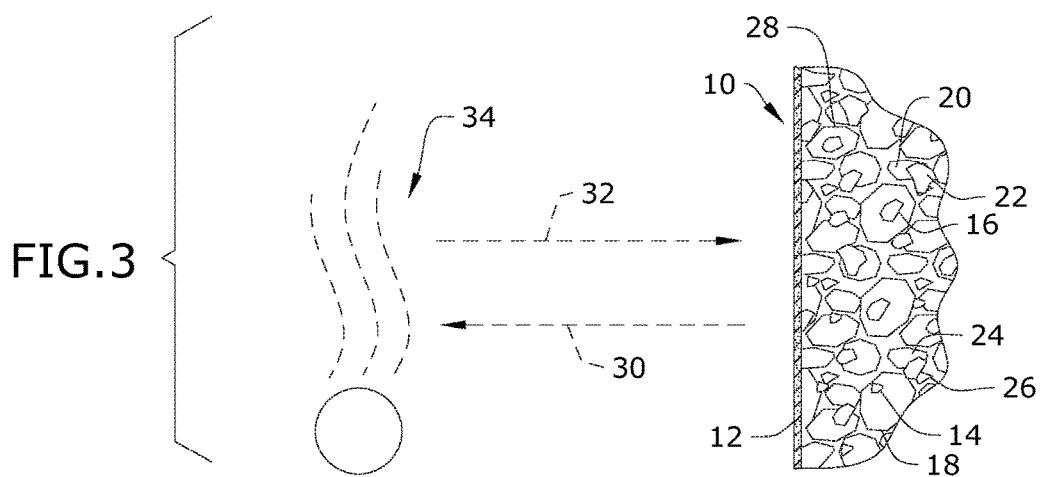

MOISTURE ABSORBENT AND DECONTAMINANT

CROSS-REFERENCE TO RELATED APPLICATION

This application claims the benefit of priority of U.S. provisional application No. 62/281,401, filed Jan. 21, 2016, the contents of which are herein incorporated by reference.

BACKGROUND OF THE INVENTION

The present invention relates to a moisture absorbent and, more particularly, to a moisture absorbent and a decontaminant.

In many items, moisture encourages the growth of mold and spoilage. Silica gel packets may be used to remove moisture. However, mold and bacteria may still grow even while using silica gel packets.

As can be seen, there is a need for an improved moisture absorbent that kills bacteria and fungus.

SUMMARY OF THE INVENTION

In one aspect of the present invention, a moisture absorbent and decontaminant comprises: a receptacle formed of a permeable material; an antimicrobial disposed within the receptacle; an antifungal disposed within the receptacle; and a moisture absorber disposed within the receptacle.

In another aspect of the present invention, a moisture absorbent and decontaminant comprises: a receptacle formed of a permeable material; a plurality of first pellets comprising an antimicrobial, wherein the plurality of first pellets are disposed within the receptacle; a plurality of second pellets comprising an antifungal, wherein the plurality of second pellets are disposed within the receptacle; and a plurality of third pellets comprising a moisture absorber, wherein the plurality of third pellets are disposed within the receptacle.

In another aspect of the present invention, a moisture absorbent and decontaminant comprises: a receptacle formed of a permeable material; a plurality of first pellets comprising an antimicrobial, wherein the plurality of first pellets are disposed within the receptacle; a plurality of second pellets comprising zinc pyrithione, wherein the plurality of second pellets are disposed within the receptacle; a plurality of third pellets comprising a nylon 6/6, wherein the plurality of third pellets are disposed within the receptacle; a plurality of fourth pellets comprising a polypropylene co-polymer, a polyethylene and a high-density polyethylene blend, wherein the plurality of fourth pellets are disposed within the receptacle; and a plurality of fifth pellets comprising a scented oil that may contain NEUTRAZINE® which is formulated to assist in counteracting malodors, wherein the plurality of fifth pellets are disposed within the receptacle.

These and other features, aspects and advantages of the present invention will become better understood with reference to the following drawings, description and claims.

BRIEF DESCRIPTION OF THE DRAWINGS

FIG. 1 is a front view of an embodiment of the present invention;

FIG. 2 is a side view of an embodiment of the present invention; and

FIG. 3 is a section detail view of an embodiment of the present invention taken along line 3-3 in FIG. 1.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

The present invention inhibits bacteria and fungus growth while absorbing moisture and offering two levels of natural odor elimination. The specially designed mesh bag that the pellets are packaged in allows the key components to get in contact with the area needing bacteria, fungus and moisture removal. The present invention kills major bacterial strains such as E-coli and Staph. The present invention removes bad odors as opposed to masking them.

The present invention may include about a 30 gram package with a blend of either: Fresh, Citrus, Pine or Vanilla AP-25 with NEUTRAZINE® and the SILIPAB-NP90382 ® with the antimicrobial and activator. The present invention works when exposed to the open environment. Only at this point does the formula kick in and start to kill bacteria and absorb moisture. The specially designed mesh bag allows the above-mentioned ingredients to escape through the small holes.

Referring to FIGS. 1 through 3, the present invention includes moisture absorbent and decontaminant 10. The moisture absorbent and decontaminant 10 includes a receptacle 12. The receptacle 12 is formed of a permeable material having a plurality of pores. The present invention includes at least first pellets 14, second pellets 16 and third pellets 18. The pellets 14, 16, 18 are enclosed within the receptacle 12. The pellets 14, 16, 18 include a diameter larger than the diameter of the pores and thereby cannot escape the receptacle 12. The first pellets 14 include an antimicrobial that emits through the pores. The second pellets 16 include an antifungal that emits through the pores. The third pellets 18 include a moisture absorber that absorbs moisture into the receptacle through the pores.

The receptacle 12 of the present invention may include a laminated porous bag and in addition, a laminated film also known as a rollstock. The porous bag or film may be formed of two sheets bonded together at the edges. Each sheet may be made of nylon mesh which has microporous polyurethane bonded to it. Alternatively, the sheets or film may be made of a fabric material such as cotton or polyester.

The antimicrobial is an agent that kills microorganisms or inhibits their growth. The antimicrobial may include, silver ions, zinc pyrithione or zinc powder. The antifungal is an agent that kills fungal cells or inhibits their growth. The antifungal may include zinc pyrithione or similar components that controls bad odors.

The present invention contains an antimicrobial agent to prevent microorganisms from degrading the product. The present invention resists odors, inhibits the growth of bacterial odors, resists microbial odor development, retards the growth and action of bacterial odors, guards against the growth of odors from microbial causes, guards against degradation from microorganisms, reduces odors from microorganisms, is odor-resistant and acts to mitigate the development of odors.

The moisture absorber of the present invention may be nylon 6/6 or similar material that is hygroscopic in nature.

The present invention may further include fourth pellets 20 disposed within the receptacle 12 which may be a filler. The filler may include polypropylene co-polymer, a polyethylene and a high-density polyethylene blend consisting of a HDPE and LLDPE blended material.

The present invention may further include fifth pellets 22, sixth pellets 24, seventh pellets 26 and eighth pellets 28. The fifth pellets 22, sixth pellets 24, seventh pellets 26 and eighth pellets 28 may each include scent oils. For example, the fifth pellets 22 may include a fresh scent oil, the sixth pellets 24 may include a citrus scent oil, the seventh pellets 26 may include a pine scent oil and eighth pellets 28 may include a vanilla scent oil.

The above pellets are mixture together to form a mixture within the receptacle. The mixture may be about 20-40 grams, such as about 30 grams total. In such embodiments, the filler may include a range of about 54% and 77.3% of the mixture, the scent may include a range of about 13.6% up to about 27.3% of the mixture, the antifungal/antimicrobial may include a range of about 4% up to about 9.1% and the moisture absorber may include a range of about 7% up to about 9.1%. For example, the mixture may include 63.6% filler, 18.2% scent, 9.1% antifungal/antimicrobial and 9.1% moisture absorber.

A method of using the present invention may include the following. The receptacle 12 is pulled out of a package and placed into the area that is needing odor removal. Having the receptacle 12 in direct contact with the problem area 34, the moisture 32 is absorbed through the pores of the receptacle 12 and the chemicals 30, such as the antifungal/antimicrobial and the scent, are emitted from the pellets and out of the pores. If left in that area 34 for three to four days, roughly 80-85% of the odor is removed and if left for an additional eight to ten days, roughly 90-95% of the odor is removed. Life expectancy of the antimicrobial and fungus inhibitor may be up to about 60 days and then the moisture absorbent and decontaminant 10 may be removed and replaced.

It should be understood, of course, that the foregoing relates to exemplary embodiments of the invention and that modifications may be made without departing from the spirit and scope of the invention as set forth in the following claims.

What is claimed is:

1. A moisture absorbent and decontaminant comprising:
   a receptacle formed of a permeable material;
   a scent oil operable to counteract malodors in a form of a plurality of pellets disposed within the receptacle;
   an antimicrobial disposed within the receptacle;
   an antifungal disposed within the receptacle; and
   a moisture absorber disposed within the receptacle.

2. The moisture absorbent and decontaminant of claim 1, wherein the receptacle is a porous bag formed of two sheets of film laminated together.

3. The moisture absorbent and decontaminant of claim 1, wherein the antimicrobial is in a form of a plurality of pellets.

4. The moisture absorbent and decontaminant of claim 1, wherein the antimicrobial is at least one of silver ions, zinc pyrithione and zinc powder.

5. The moisture absorbent and decontaminant of claim 1, wherein the antifungal is in a form of a plurality of pellets.

6. The moisture absorbent and decontaminant of claim 1, wherein the antifungal is zinc pyrithione.

7. The moisture absorbent and decontaminant of claim 1, wherein the moisture absorber is in a form of a plurality of pellets.

8. The moisture absorbent and decontaminant of claim 1, wherein the moisture absorber is nylon 6/6.

9. The moisture absorbent and decontaminant of claim 1, further comprising a polypropylene co-polymer, a polyethylene and a high-density polyethylene blend in a form of a plurality of pellets disposed within the receptacle.

10. The moisture absorbent and decontaminant of claim 1, wherein the scent oil is selected from the group consisting of a fresh scent oil, a citrus scent oil, a pine scent oil and a vanilla scent oil.

11. A moisture absorbent and decontaminant comprising:
    a receptacle formed of a permeable material;
    a plurality of first pellets comprising an antimicrobial, wherein the plurality of first pellets are disposed within the receptacle;
    a plurality of second pellets comprising zinc pyrithione, wherein the plurality of second pellets are disposed within the receptacle;
    a plurality of third pellets comprising a nylon 6/6, wherein the plurality of third pellets are disposed within the receptacle;
    a plurality of fourth pellets comprising a polypropylene co-polymer, a polyethylene and a high-density polyethylene blend, wherein the plurality of fourth pellets are disposed within the receptacle; and
    a plurality of fifth pellets comprising a scent oil, wherein the plurality of fifth pellets are disposed within the receptacle.

12. The moisture absorbent and decontaminant of claim 11, wherein the receptacle is a porous bag formed of two sheets of film laminated together.

13. A moisture absorbent and decontaminant comprising:
    a receptacle formed of a permeable material;
    a polypropylene co-polymer, a polyethylene and a high-density polyethylene blend in a form of a plurality of pellets disposed within the receptacle;
    an antimicrobial disposed within the receptacle;
    an antifungal disposed within the receptacle; and
    a moisture absorber disposed within the receptacle.

* * * * *